United States Patent
Flock (10) Patent No.: US 9,506,871 B1
(45) Date of Patent: Nov. 29, 2016

(54) PULSED LASER INDUCED PLASMA LIGHT SOURCE

(71) Applicant: KLA-Tencor Corporation, Milpitas, CA (US)

(72) Inventor: Klaus Flock, Sunnyvale, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/578,949

(22) Filed: Dec. 22, 2014

Related U.S. Application Data (60) Provisional application No. 62/002,881, filed on May 25, 2014.

(51) Int. Cl.
  *G01N 21/00* (2006.01)
  *G01N 21/88* (2006.01)
  (Continued)

(52) U.S. Cl.
  CPC ........... *G01N 21/8806* (2013.01); *F21K 99/00* (2013.01); *G01N 21/9501* (2013.01);
  (Continued)

(58) Field of Classification Search
  CPC ......... C23C 16/18; H01S 3/10; H05G 2/003; H05G 2/00; H05H 1/24; G03F 7/20; H01J 61/20; H01J 61/00; H01J 35/20
  USPC ............. 356/237.2–237.6, 51, 369; 250/288, 250/493.1, 287
  See application file for complete search history.

(56) References Cited

U.S. PATENT DOCUMENTS

| 4,866,517 A | 9/1989 | Mochizuki et al. |
| 5,608,526 A | 3/1997 | Piwonka-Corle et al. |

(Continued)

FOREIGN PATENT DOCUMENTS

| CN | 202351175 U | 7/2012 |
| EP | 418785 B1 | 6/2008 |

(Continued)

OTHER PUBLICATIONS

L. Poncea, et al., Laser Induced Breakdown Spectroscopy: Advances in Resolution and Portability, RCF vol. 27, No. 1, 2010, p. 94.

(Continued)

*Primary Examiner* — Tarifur Chowdhury
*Assistant Examiner* — Isiaka Akanbi
(74) *Attorney, Agent, or Firm* — Spano Law Group; Joseph S. Spano (57) ABSTRACT

Methods and systems are described herein for producing high radiance illumination light suitable for semiconductor metrology. A cold gas is repeatedly ignited by a pulsed laser to periodically generate accessible, high brightness illumination light generated during each break-down event. The pulse duration and repetition period are set to ignite, but not sustain fully formed plasma. The central plasma core emits high color temperature light before a cooler plasma region forms around the central core. Thus, after ignition, the plasma is extinguished before the arrival of the next laser pulse. The repeated plasma ignition/extinction cycle generates illumination light at high color temperature that is accessible for illumination purposes in a metrology application. In one embodiment, a bulb filled with Xenon gas at 10 atmospheres is repeatedly ignited with a pulsed laser having pulse duration of 10 nanoseconds to generate illumination light with a color temperature of approximately 60,000 Kelvin.

34 Claims, 4 Drawing Sheets

(51) Int. Cl.
*G01N 21/95* (2006.01)
*G01N 21/956* (2006.01)
*F21K 99/00* (2016.01)
*H05H 1/46* (2006.01)
*G02B 27/09* (2006.01)

(52) U.S. Cl.
CPC ............ *G01N21/956* (2013.01); *G02B 27/09* (2013.01); *H05H 1/46* (2013.01); *G01N 2021/95676* (2013.01); *G01N 2201/0697* (2013.01)

(56) References Cited

U.S. PATENT DOCUMENTS

| | | | |
|---|---|---|---|
| 5,859,424 | A | 1/1999 | Norton et al. |
| 6,429,943 | B1 | 8/2002 | Opsal et al. |
| 7,368,741 | B2 | 5/2008 | Melnychuk et al. |
| 7,478,019 | B2 | 1/2009 | Zangooie et al. |
| 7,786,455 | B2 | 8/2010 | Smith |
| 7,928,416 | B2 | 4/2011 | Fomenkov |
| 7,933,026 | B2 | 4/2011 | Opsal et al. |
| 8,035,092 | B2 | 10/2011 | Bykanov et al. |
| 8,198,615 | B2 | 6/2012 | Bykanov et al. |
| 8,242,695 | B2 | 8/2012 | Sumitomo et al. |
| 8,283,643 | B2 | 10/2012 | Partlo et al. |
| 8,598,549 | B2 | 12/2013 | Bowering et al. |
| 8,604,452 | B2 | 12/2013 | Ershov |
| 8,653,437 | B2 | 2/2014 | Partlo et al. |
| 2009/0032740 | A1* | 2/2009 | Smith .................... B82Y 10/00 250/503.1 |
| 2013/0164457 | A1 | 6/2013 | Ehlers et al. |
| 2013/0321810 | A1 | 12/2013 | Wang et al. |
| 2013/0329204 | A1 | 12/2013 | Pellemans et al. |
| 2013/0342105 | A1* | 12/2013 | Shchemelinin ... H01J 37/32055 315/111.21 |
| 2014/0111791 | A1 | 4/2014 | Manassen et al. |
| 2014/0172394 | A1 | 6/2014 | Kuznetsov et al. |
| 2014/0222380 | A1 | 8/2014 | Kuznetsov et al. |

FOREIGN PATENT DOCUMENTS

| | | |
|---|---|---|
| JP | H10221499 A | 8/1998 |
| JP | 2008130988 A | 6/2008 |

OTHER PUBLICATIONS

Babankova, Dagmar, et al., Optical and X-Ray Emission Spectroscopy of High-Power Laser-Induced Dielectric Breakdown in Molecular Gases and Their Mixtures, J. Phys. Chem. A 2006, 110, 12113-12120.

Hugenschmidt, M., et al. Schlieren-Cinematographic and Holograph Diagnostic of Laser-Produced Plasma in Xenon, Applied Optics, vol. 11, No. 2, Feb. 1972, pp. 339-344.

* cited by examiner

PULSED LASER INDUCED PLASMA LIGHT SOURCE

CROSS REFERENCE TO RELATED APPLICATION

The present application for patent claims priority under 35 U.S.C. §119 from U.S. provisional patent application Ser. No. 62/002,881, entitled "Pulsed Plasma Light Source," filed May 25, 2014, the subject matter of which is incorporated herein by reference.

TECHNICAL FIELD

The described embodiments relate to optical metrology and inspection systems for microscopy, and more particularly to optical metrology and inspection systems involving plasma based radiation sources.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. In the field of semiconductor metrology, a metrology tool includes an illumination system which illuminates a target, a collection system which captures relevant information provided by the illumination system's interaction (or lack thereof) with a target, and a processing system which analyzes the information collected using one or more algorithms. Metrology tools can be used to measure structural and material characteristics (e.g., material composition, dimensional characteristics of structures and films such as film thickness and/or critical dimensions of structures, overlay, etc.) associated with various semiconductor fabrication processes. These measurements are used to facilitate process controls and/or yield efficiencies in the manufacture of semiconductor dies.

Bright field (BF) and dark field (DF) metrology modalities may be used to measure specular or quasi-specular surfaces such as semiconductor wafers. BF metrology systems position collection optics to capture a substantial portion of the light spectrally reflected by the surface under inspection. DF metrology systems position collection optics substantially out of the path of the spectrally reflected light such that the collection optics capture light scattered by objects on the surface being measured. Viable metrology systems, particularly systems employing a BF measurement modality, require high radiance illumination and a high numerical aperture (NA) to maximize the defect sensitivity of the system. In general, the defect sensitivity of a metrology system is proportional to the wavelength of the illumination light divided by the NA of the objective. Without further improvement in NA, the overall defect sensitivity of current metrology tools is limited by the wavelength of the illumination source.

In some examples, current metrology systems employ an electrode-based, relatively high intensity discharge arc lamp to generate illumination light. These arc lamps include an anode and cathode to excite a working medium (typically xenon or mercury gas) contained within a chamber of the lamp. An electrical discharge is generated between the anode and cathode to provide power to the excited (e.g., ionized) gas to sustain light emission from the ionized gas during operation of the light source. However, these light sources have a number of disadvantages. For example, electrode based, relatively high intensity discharge arc lamps have radiance limits and power limits due to electrostatic constraints on current density from the electrodes, the limited emissivity of gases as black body emitters, the relatively rapid erosion of electrodes made from refractory materials due to the presence of relatively large current densities at the cathodes, and the inability to control dopants (which can lower the operating temperature of the refractory cathodes) for relatively long periods of time at the required emission current. As a result, state of the art xenon-based arc lamps typically generate light with a color temperature that is limited to approximately 6,000 degrees Kelvin.

In some other examples, laser sustained plasma based light sources have been developed. An exemplary laser sustained plasma system is described in U.S. Pat. No. 7,786,455 assigned to Energetiq Technology Inc. In one example, a xenon lamp is ignited with a high voltage pulse applied through electrodes. Once started, the plasma is continuously sustained with a powerful continuous-wave (CW) laser beam focused to a small spot inside the Xenon gas envelope. However, laser sustained plasma light sources also face significant limitations. The laser sustained plasma develops a temperature gradient across the plasma (i.e., a hot central core surrounded by cooler outer portions) that causes self-absorption; particularly absorption of short wavelength light. As a result, it is difficult to increase the accessible plasma temperature beyond approximately 12,000-15,000 degrees Kelvin. Moreover, an increase in laser power generally results in a larger plasma size that has a diminishing impact on color temperature.

In addition, state of the art light sources that employ electrodes must arrange the long axis of the lamp perpendicular to the gravitational field to achieve an acceptable signal to noise ratio (SNR). Unfortunately, certain metrology system architectures (e.g., broadband spectroscopic ellipsometers) employ a rectangular illumination slit (e.g., polarizer slit) that is not aligned perpendicular to the gravitational field. In these systems, the long axis of the illumination slit and the long axis of the plasma are currently crossed. This results in loss of light, higher source non-uniformity across the polarizer slit, and higher sensitivity to residual wedges in rotating elements, such as a polarizing prism.

In some other examples, light sources employing laser produced plasma have been developed for lithographic applications. An exemplary extreme ultraviolet (EUV) light source is described in U.S. Pat. No. 7,368,741 assigned to Cymer, Inc. In one example, a working medium at low pressure is pre-ionized by a radiofrequency coil, ignited with a focused laser beam, and sustained by a combination of the focused laser beam and electrical discharge to generate a pinch plasma that emits EUV light. Generation of illumination suitable for EUV lithography requires emission along narrow atomic lines, rather than broadband emission. As a result, EUV illumination sources generate plasma in a low pressure (i.e., vacuum) environment to minimize reabsorption and broadening of the desired EUV emission lines. The low pressure environment allows the plasma to expand into a large volume, corresponding to a mean-free-path between collisions. If relatively high pressures were employed (e.g., 0.5 atmosphere, or greater), these sources would fail to generate any useable amount of EUV light. Large plasma volumes are acceptable for an EUV source that focuses on the generation of as much EUV emission along atomic lines as possible. However, in a metrology application, high radiance, broadband radiation is required. The large plasmas generated by systems designed for EUV emission suffer from low brightness and narrow band emission that does not fulfill the requirement for broadband, high brightness illumination in metrology applications.

In some other examples, laser induced break-down of the target is employed for analysis of the target itself. In these examples, a pulsed laser is used to evaporate a small amount of material from a specimen. The resulting plasma radiation is spectrally analyzed to reveal properties of the specimen. This technique is commonly referred to as Laser Induced Breakdown Spectroscopy (LIBS) and Laser Induced Plasma Spectroscopy (LIPS). In these applications, laser induced breakdown of the target itself is used to gain insight into the chemical composition of the target. However, no consideration is given to the use of the emission from the primary target to illuminate another, secondary target for purposes of analyzing properties of the secondary target based on its interaction with the emitted light.

Existing laser based plasma illumination sources are limited in brightness and reliability for metrology applications. Thus, improved methods and systems for generating and extracting high brightness, broadband light at suitable flux levels are desired.

SUMMARY

Methods and systems are described herein for producing high radiance illumination light suitable for semiconductor metrology. A cold gas is repeatedly ignited by a pulsed laser to periodically generate accessible, high brightness illumination light generated during each break-down event. The pulse duration and repetition period are set to ignite, but not sustain a fully formed plasma. After ignition, the plasma is left to extinguish before the arrival of the next laser pulse. The repeated plasma ignition/extinction cycle generates illumination light at high color temperature.

In one embodiment, a pulsed laser illumination source generates a pulsed output beam that passes through a beam expanding optic and a condensing optic configured to focus the laser illumination at the location of plasma formation with high numerical aperture (NA). The NA of the focusing system is chosen according to a power density requirement for plasma ignition by dielectric break-down, i.e., to concentrate the pump laser power within a sufficiently small volume. In some embodiments, the optical elements are configured to generate an NA greater than 0.6. The pulsed output beam has a pulse duration, $T_P$, and a repetition period, $T_R$. At the point of interaction with a working medium, high electromagnetic field strengths are realized during the pulse period to induce break-down and plasma formation. In some embodiments, a power density of approximately 10 GW/cm$^2$ in a xenon gas environment at 10 atmospheres will initiate plasma formation.

In one aspect, the pulse duration is selected to initiate plasma formation, but not sustain a fully formed plasma. In this manner, high brightness light may be accessed before formation of the steady-state plasma induces substantial self-absorption that reduces the color temperature of the accessible light. In one example, at the point of plasma ignition, the accessible light has a color temperature greater than 30,000 degrees Kelvin. In some examples, the color temperature of the accessible light is greater than 60,000 degrees Kelvin. In some examples, the pulse duration, $T_P$, is less than 200 nanoseconds. In some examples, the pulse duration, $T_P$, is less than 20 nanoseconds.

The ignition process is repeated at the repetition period, $T_R$, of the pulsed laser illumination source 110. Sufficient time is allowed to elapse for the previously ignited plasma to extinguish before initiating another plasma. Because the plasma is allowed to extinguish before re-ignition, the accessible light output from the plasma emission is periodic with a modulation depth greater than ninety percent. In some embodiments, the modulation depth of the accessible light output from the plasma emission is greater than ninety-nine percent. In some embodiments, the modulation depth of the accessible light output from the plasma emission is effectively one hundred percent. In some embodiments, the repetition period, $T_R$, is at least 0.1 microseconds. In some embodiments, the repetition period, $T_R$, is at least 1 microsecond. In some other embodiments, the repetition period is greater than 10 ns. In some other embodiments, the repetition period is greater than 20 ns. In general, the repetition period is determined based on the plasma life-time. The plasma life-time is typically on the order of 10 to several 100 nanoseconds. The repetition period is also based on the power and repetition rate capabilities of the pulsed drive laser. The accessible illumination light is broadband, including spectral components from less than 200 nanometers to greater than 1,500 nanometers.

In some embodiments, xenon gas is selected as the working medium due to its low ionization energy. In some embodiments, the working medium includes xenon gas mixed with one or more other gaseous species, or spurious amounts of a secondary species, such as a metal vapor or a small amount of radio-active material. In some embodiments, the working medium is a liquid or solid material that is transparent to the radiation generated by the pump laser.

In another aspect, the ratio of atomic-line emission to blackbody emission from the plasma ignition process is controlled by selection of particular operational parameters, such as pulse duration, $T_P$, pulse energy, pulse repetition period, $T_R$, working medium pressure, and average working medium temperature.

In some embodiments, the plasma is ignited based solely on the electromagnetic field induced by the pulsed laser beam. However, in another aspect, the plasma ignition process may be facilitated by pre-ionization of the working medium. In some embodiments, the plasma ignition process is facilitated by cold-cathode emission of electrons. In some embodiments, the plasma ignition process is facilitated by an ionization source, such as a DUV light-source, or laser, operating concurrently with the pulsed laser illumination source.

In another aspect, a metrology or inspection system suitable for measurement of wafers or reticles includes a repeatedly induced plasma light source as described herein. In some examples, the high brightness illumination light can improve the performance of Spectroscopic Ellipsometry (SE), Spectroscopic Reflectometry (SR), and Beam-Profile Reflectometry (BPR) systems used in film, critical dimension (CD), and composition metrology. Furthermore, the high brightness illumination source described herein can improve the performance of wafer and mask inspection systems employed to detect defects of various types and sizes.

In one further aspect, a metrology or inspection system is configured to synchronize the output of the repeatedly induced plasma light source with the operation of another component of system such as a detector, a rotating element such as a rotating polarizer, rotating compensator, rotating analyzer, etc., a specimen positioning system, or another component. In some embodiments, the output of the repeatedly induced plasma light source is synchronized with the readout of a multi-sensor detector to eliminate mixing of signals while charges are being transferred during readout. In some embodiments, the output of the repeatedly induced plasma light source is synchronized with the readout of a single-sensor detector.

In another further aspect, the metrology or inspection system is configured to align and move the location of the induced plasma with respect to an illumination aperture of the system. In some embodiments, the focal point of the pulsed output beam is moved during the time between one or more pulses so that the illumination light generated by each plasma ignition, or group of plasma ignitions, illuminates a different part of an illumination aperture of the system. In a further aspect, data collected by the detector is averaged over the sequence of pulses that range over the illumination aperture. In some embodiments, a scanning mirror located in the optical beam path between the pulsed laser illumination source and the induced plasma is moved to redirect the pulsed output beam to different locations within the volume of the working medium.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems are described herein for producing high radiance illumination light for use in semiconductor metrology based on repeatedly induced plasma ignition. More specifically, a cold gas is repeatedly ignited by a pulsed laser at a given interval to periodically generate bright plasma. The laser induced plasma light source repeatedly achieves dielectric break-down in a gaseous atmosphere by multi-photon absorption and inverse Bremsstrahlung. A pulse of laser light triggers a break-down event that induces a phase transition from an ordinary state of matter to a plasma state, thus triggering emission of light at high color temperature. After the pulse of laser light, the plasma is extinguished due to a lack of pump energy. This results in a phase transition back to the ordinary state of matter. After the phase transition back to the ordinary state of matter, the plasma ignition/extinction cycle is repeated. A subsequent laser light pulse triggers another break-down event that generates light, followed by an extinction period. In this manner, light output is periodically generated during the break-down events of a repeated, pulsed laser induced plasma ignition/extinction cycle. Because the plasma is allowed to extinguish before re-ignition, the accessible light output from the plasma emission is periodic with a modulation depth greater than ninety percent. In some embodiments, the modulation depth of the accessible light output from the plasma emission is greater than ninety-nine percent. In some embodiments, the modulation depth of the accessible light output from the plasma emission is effectively one hundred percent.

During the initial stages of the plasma formation process, the central core of the laser induced plasma emits light at a high color temperature. However, since the plasma has not yet had time to fully develop, the light is able to radiate from the plasma without reabsorption because the hot-plasma core is not yet surrounded by a cooler outer plasma region. Thus, the optimal time to access high color temperature light from a laser induced plasma is in its initial stages of formation (e.g., at the time of break-down initiation), rather than after the plasma has had time to fully develop. This increases the color temperature of accessible light for optical metrology and inspection applications. Accessible light is not self-absorbed and is available for collection and use, for example, in a metrology system. In some examples, accessible light emitted from a repeatedly ignited plasma light source is greater than 30,000 degrees Kelvin. In some examples, accessible light with a color temperature of at least 60,000 degrees Kelvin is generated.

In contrast, a laser sustained plasma is ignited and sustained as a fully formed plasma. The fully formed plasma includes a central core surrounded by a cooler plasma region. This cooler plasma region absorbs a portion of the light emitted from the central core, and particularly short wavelength light. In this manner, the color temperature of accessible light emitted from a light source based on sustained plasma, whether sustained by a continuous wavelength or pulsed laser source, is limited.

Figure 1:
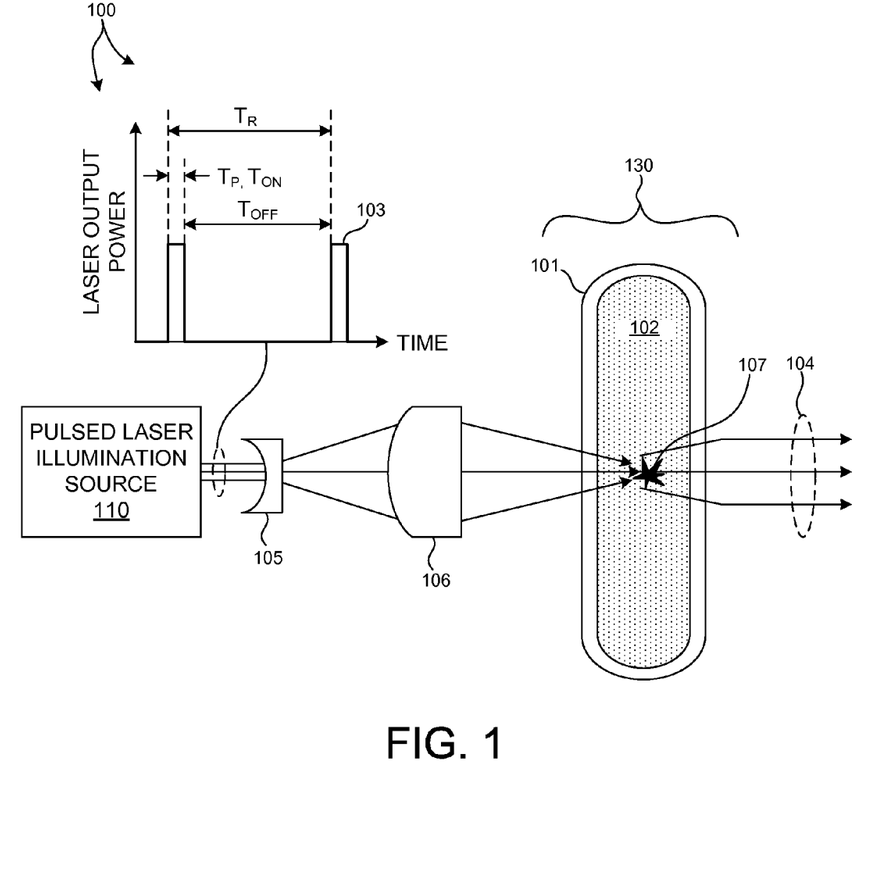
FIG. 1 illustrates an embodiment of a repeatedly induced plasma light source (RIPLS) 100 configured in accordance with at least one aspect of the present invention.

FIG. 1 illustrates an embodiment of a repeatedly induced plasma light source (RIPLS) 100 configured in accordance with at least one aspect of the present invention. RIPLS 100 includes a laser illumination source 110 and a plasma bulb 130 including a working medium 102. In the depicted embodiment, a plasma bulb 130 includes at least one wall 101 formed from a material (e.g., glass) that is substantially transparent to at least a portion of the pulsed output beam 103 generated by laser illumination source 110. Similarly, the at least one wall is also substantially transparent to at least a portion of the accessible illumination 104 (e.g., IR light, visible light, ultraviolet light) emitted by the plasma 107 ignited within the plasma bulb 130. For example, the wall 101 may be transparent to a particular spectral region of the broadband emission 104 from the plasma 107.

In one embodiment, the working medium 102 of the plasma bulb 130 may include an inert gas (e.g., noble gas or non-noble gas) or a non-inert gas (e.g., mercury vapor) or their mixtures. For example, it is anticipated herein that the volume of working medium of the present invention may include xenon. For instance, the working medium may include a substantially pure xenon gas held at pressure in excess of 5 atmospheres. In another instance, the working medium may include a substantially pure krypton gas held at pressure in excess of 5 atmospheres. In general, the plasma bulb 130 may be filled with any gas known in the art suitable for use in a repeatedly induced plasma light source. By way of non-limiting example, the working medium may include any one or combination of Ar, Kr, Xe, He, Ne, $N_2$, $Br_2$, $Cl_2$, $I_2$, $H_2O$, $O_2$, $H_2$, $CH_4$, NO, $NO_2$, $CH_3OH$, $C_2H_5OH$, $CO_2$, $NH_3$, one or more metal halides, a Ne/Xe mixture, an Ar/Xe mixture, a Kr/Xe mixture, an Ar/Kr/Xe mixture, an ArHg mixture, a KrHg mixture, and a XeHg mixture. In general, the present invention should be interpreted to extend to any light pumped plasma generating system and should further be interpreted to extend to any type of working medium suitable for initiating a plasma.

Plasma bulb 130 may be formed from a variety of glass or crystalline materials. In one embodiment, the glass bulb may be formed from fused silica glass. In some embodiments, the plasma bulb 130 may be formed from a low OH content fused synthetic quartz glass material. In other embodiments, the plasma bulb 130 may be formed from a high OH content fused synthetic silica glass material. For example, the plasma bulb 130 may include, but is not limited to, SUPRASIL 1, SUPRASIL 2, SUPRASIL 300, SUPRASIL 310, HERALUX PLUS, and HERALUX-VUV. In some embodiments, a glass material forming the plasma bulb 130 may be doped with fluorine, hydrogen, etc. Various glasses suitable for implementation in the plasma bulb of the present invention are discussed in detail in A. Schreiber et al., Radiation Resistance of Quartz Glass for VUV Discharge Lamps, J. Phys. D: Appl. Phys. 38 (2005), 3242-3250, which is incorporated herein in the entirety. In some embodiments, the plasma bulb 130 may be formed from a crystalline material such as a crystalline quartz material, a sapphire material, calcium fluoride, or magnesium fluoride.

In the illustrated embodiment, plasma bulb 130 includes a cylindrical shape with spherical ends. In some embodiments, plasma bulb 130 includes any of a substantially spherical shape, a substantially cylindrical shape, a substantially ellipsoidal shape, and a substantially prolate spheroid shape. These shapes are provided by way of non-limiting example. Many other shapes may be contemplated.

In some other embodiments, working medium 102 is not contained in a bulb, but is included in a reflective chamber configured to collect light radiated from the plasma for illumination of a specimen undergoing measurement. In these embodiments, the optical path from the plasma to the specimen under inspection includes reflective elements, but does not include transmissive elements. These embodiments may be preferred when transmission of short wavelength light (e.g., less than 200 nanometers) is desired without the optical losses that are inherent in the transmission of short wavelength light through solid media (e.g., lenses, windows, etc.).

In some other embodiments, the working medium may be a liquid or solid material. In some examples, it may be advantageous to focus the pulsed excitation light within a liquid or solid material that is substantially transparent to the focused, pulsed excitation light. For example, plasma initiation may be achieved at lower power densities due to the relatively high material densities of liquid or solid materials. In another example, a liquid material may be preferred due to its ability to self-repair the volume of a plasma damaged spot. In another example, a plasma may be initiated within a target that includes, or is encapsulated by, a liquid or solid material such that the material under investigation is not exposed to ambient environmental conditions. In this manner, material studies, such as those achieved by laser induced breakdown spectroscopy, can be conducted in an isolated environment. A plasma initiated within a solid or liquid material is not suitable for coupling out sharp atomic lines of radiation due to the relatively high density of the surrounding material. However, such a light source is able to generate accessible, high brightness illumination light.

In a further aspect, a liquid or solid working medium may be shaped to facilitate the focusing of pulsed excitation light into the target. For example, the liquid or solid working medium may be spherical in shape to reduce optical aberration, and act as a focusing lens for the pulsed excitation light.

Pulsed laser illumination source 110 is configured to generate a pulsed output beam 103 that passes through a beam expanding optic 105 and a condensing optic 106 configured to focus the laser illumination at the location of plasma 107 with high numerical aperture (NA). In some embodiments, the optical elements are configured to generate a NA greater than 0.6. To locate condensing optic 106 within a reasonable working distance from plasma 107 (e.g., few centimeters) at high NA (e.g., greater than 0.6), a beam expanding optic 105 is employed. In some embodiments, beam expanding optic 105 is configured to expand the diameter of the incoming beam by 200 times, or more, at incidence with the condensing optic 106.

Pulsed laser illumination source 110 is configured to generate a pulsed output beam 103 having a pulse duration, $T_P$, and a repetition period, $T_R$. Hence, the output beam 103 of the pulsed laser illumination source 110 includes an on-time, $T_{on}$, corresponding to the pulse duration, $T_P$, and an off-time, $T_{off}$, corresponding to the difference between the pulse duration, $T_P$, and the pulse repetition period, $T_R$. At the point of interaction with working medium 102, high electromagnetic field strengths are realized during the pulse period to induce break-down and plasma formation. This is achieved by focusing the pulsed output beam 103 with sufficiently high peak-power to a small spot within the envelope of plasma bulb 130. Pulse duration refers to the period of time, $T_P$, elapsed during a pulse of output beam 103. A laser pump pulse is in general a function of time with a sharp on-set and characteristic peak-power, followed by an approximately exponential decay. A laser pulse duration is understood in relation to the shape of the pump pulse and, for instance, can be defined as the duration where the output is greater than $1/e^2$ of peak power. The pulse repetition period, $T_R$, refers to the time elapsed between, for example, the rising edge (or falling edge) of each pulse of output beam 103. In general, the pulse repetition period is the inverse of the repetition rate of the pulsed laser illumination source 110.

In some embodiments, a power density of approximately 10 $GW/cm^2$ in a xenon gas environment at 10 atmospheres will initiate plasma formation. However, in some other embodiments, plasma formation is initiated at power densities less than 10 $GW/cm^2$. In one example, break-down in Xenon was achieved with a 532 nanometer laser source with a power density of 8 $GW/cm^2$. This example is described in "Laser-induced plasma formation in Xe, Ar, $N_2$, and $O_2$ at the first four Nd:YAG harmonics," by Jon P. Davis, et al., Applied Optics, Vol. 30, Issue. 30, pp. 4358-4364 (1991), the content of which is incorporated herein by reference in its entirety. In general, power densities on the order of 10-1000 GW/cm² may be employed to initiate plasma formation.

In one aspect, the pulse duration is selected to initiate plasma formation, but not sustain a fully formed plasma. In this manner, high brightness light may be accessed before formation of the steady-state plasma induces substantial self-absorption that reduces the color temperature of the accessible light. In one example, at the point of plasma ignition, the accessible light has a color temperature greater than 30,000 degrees Kelvin. In some examples, the color temperature of the accessible light is greater than 60,000 degrees Kelvin. Typically, the pulse duration is on the order of 10-100 nanoseconds. Pulse durations greater than 100 nanoseconds may be employed to lower the effective color temperature of the plasma. Pulse durations could be less than 10 nanoseconds to increase the effective color temperature. In general, increasing the pulse duration will shift the average color temperature and plasma size closer to steady state plasma conditions during each excitation/extinction cycle. Conversely, decreasing the pulse duration increases average color temperature and reduces average plasma size during each excitation/extinction cycle. In some examples, the pulse duration, $T_P$, is less than 20 nanoseconds. In some examples, the pulse duration, $T_p$, is less than 10 nanoseconds. For a given application, there could be a preferred pulse duration that optimizes the effective color temperature, effective plasma size, and required power density of the pump laser.

In a further aspect, a pulsed laser illumination source as described herein, is further configured to adjust the pulse duration to achieve a desired average color temperature of the accessible light output from the plasma emission. In one example, a command signal 136 is communicated to pulsed laser illumination source 110. In response, the pulse duration of the pulsed laser illumination source is adjusted to achieve a desired average color temperature of the accessible light output 104 from the plasma emission.

The ignition process is repeated at the repetition period, $T_R$, of the pulsed laser illumination source 110. Sufficient time should elapse to allow for the previously ignited plasma to extinguish before initiating another plasma. In some embodiments, the repetition period, $T_R$, is at least 0.1 microseconds. In some embodiments, the repetition period, $T_R$, is at least 1 microsecond.

Because the plasma is allowed to extinguish before reignition, the accessible light output from the plasma emission is periodic with a modulation depth greater than ninety percent. In other words, the spectral power of the accessible light output at its minimum is at least 90% less than the spectral power of the accessible light output at its maximum for any given excitation/extinction cycle. In some embodiments, the modulation depth of the accessible light output from the plasma emission is greater than ninety-nine percent. In some embodiments, the modulation depth of the accessible light output from the plasma emission is effectively one hundred percent. In this manner, a pulse of accessible illumination light 104 is emitted from a periodically generated plasma state 107. The illumination light 104 is broadband, including spectral components from less than 200 nanometers to greater than 1,500 nanometers. In some examples, the emission ranges from at least 150 nanometers to more than 2500 nanometers. Depending on the system configuration, spectral emission may be in the ranges including 120 nm to 190 nm, 190 nm to 860 nm, 175 nm to 860 nm, 175 nm to 2200 nm, 190 nm to 1700 nm, or 120 nm to 2500 nm.

In general, the average power of illumination light 104 is inversely proportional to the repetition period, $T_R$, of the pulsed laser illumination source 110 (proportional to the repetition rate), and the spectral distribution of illumination light 104 is substantially constant over a wide range of repetition periods. The repetition rate multiplied by the energy per pulse equals the average power. For example, a laser that generates 1,000 Microjoules per pulse at a repetition rate of 1 Megahertz has 1,000 Watts average power output.

The feasibility of repeated ignition has been confirmed at repetition rates of 5 Hz, 50 Hz, 100 Hz, 500 Hz, and 1000 Hz, using a 527 nm, actively Q-switched, frequency doubled, pulsed laser with maximum peak-power 12.5 kW and an average power of less than 5 Watts.

In another aspect, the ratio of atomic-line emission to blackbody emission from plasma 107 is controlled by selection of particular operational parameters, such as pulse duration, $T_P$, pulse energy, pulse repetition period, $T_R$, and working medium pressure.

Changes from an initial state of matter to a plasma state are governed by the laws of thermodynamics with a dependency on working medium pressure, temperature, and atomic number.

In some embodiments, the pressure of working medium 102 is adjusted to influence the optical power density required to initiate a phase transition, the plasma size, and the ratio of broadband spectral output to output along atomic lines. In general, an increase in working medium pressure reduces the optical power density required to initiate a phase transition, confines the plasma size, and increases the ratio of broadband spectral output to output along atomic lines. These effects are all desirable from the point of view of generation of illumination light employed in metrology and inspection applications. Smaller plasma sizes yield higher brightness, and achieving broadband spectral output from a single source is highly desirable. In some examples, repeated plasma ignition has been achieved with plasma bulb 130 filled with xenon working medium at a fill pressure of approximately 10 atmospheres. In some examples, the pressure of working medium 102 is at least one atmosphere. In some other examples, the pressure of working medium 102 is at least 10 atmospheres. In general, higher pressures result in a broadened spectrum and a more confined plasma hot-spot. In addition, higher pressures reduce the minimum required power density to initiate plasma formation. Since, an increase in the pressure of the working medium reduces the required energy per pulse, the power requirement on the laser is lowered for a given repetition rate. For an optical metrology application, is may be desirable to maximize the available gas-pressure, minimize the required power density of the pump laser, and maximize the available repetition rate of the pump laser.

In some embodiments, the average temperature of the working medium (e.g., Xenon gas) is adjusted to influence the optical power density required to initiate a phase transition from an ordinary state of matter into the plasma state. In general, an increase in the average temperature of the working medium reduces the optical power density required to initiate a phase transition.

The transition from an ordinary state of matter to a plasma state depends on the ionization energy of the working medium or gas mixture. This, in turn, depends on the electron configuration of the working medium or gas mixture. In some embodiments, xenon gas is selected as working medium 102 due to its low ionization energy. In some embodiments, working medium 102 is pure xenon gas. In some other embodiments, working medium 102 includes xenon gas mixed with one or more other gaseous species.

In a further aspect, working medium 102 also includes spurious amounts of a secondary species, such as a metal vapor. The presence of these species may facilitate breakdown at lower electromagnetic field strength. In some embodiments, working medium 102 includes xenon gas mixed with a small amount of radio-active material.

In some embodiments, plasma 107 is ignited based solely on the electromagnetic field induced by pulsed output beam 103. However, in another aspect, the plasma ignition process may be facilitated by pre-ionization of the working medium 102. In some embodiments, the plasma ignition process is facilitated by cold-cathode emission of electrons. In some embodiments, the plasma ignition process is facilitated by an ionization source, such as a DUV light-source, radio-active element, a laser operating concurrently with pulsed laser illumination source 110.

The plasma generated by a laser driven plasma system is conjugate to an output of the drive laser. As such, a portion of light propagates back towards the laser cavity, and includes constituents of either, or both, light from the generated plasma and laser light reflected by the conductive plasma. To achieve low noise operation of a broad-band light source in optical metrology applications, measures are taken to reduce the sensitivity of laser output to back-propagating constituents, or reduce the amount of back-propagating constituents. In a CW-pumped plasma system, a portion of the light propagated from the laser to the plasma is reflected by the plasma back toward the drive laser. This feedback of electromagnetic radiation from the plasma volume to the drive laser is undesirable as it tends to have a destabilizing effect on the drive laser. In some laser sustained plasma systems, a cold mirror is located in collimated space to substantially suppress feedback to the drive laser and accompanying delivery optics. This adds cost and optical losses to the system.

In another aspect, the pulse duration, $T_P$, of a RIPLS system is selected to be short relative to the plasma formation time. Thus, reflection of a portion of the pump energy by existing plasma is substantially absent compared to a CW-sustained light-source. Further, a pulsed laser, such as a Q-switched laser, is inherently less sensitive to optical feedback compared to a CW laser, since the active material of the laser is nearly fully saturated (inverted) before lasing is initiated. During output, the reservoir is emptied in an avalanche of stimulated emission until the inverted states are substantially depleted beyond a lasing threshold. In this mode of operation, concern for output power stability of a CW laser does not apply. Instead, we are concerned with pulse-to-pulse variation of output energy. Mode noise concerns are retained for both CW- and pulsed laser operation.

In some embodiments, the pulse repetition period and the geometry of the volume of working medium are selected to achieve a desired phasing of shock-waves generated by the laser pulse. In general, shock-waves generated by the laser pulse are managed such that they do not induce excessive noise, or cause catastrophic failure. However, by tuning the pulse repetition rate and the geometry of the working medium (e.g., geometry of a container holding the working medium), the reflected shock wave can be used to further compress the working medium in the focal volume at the time of arrival of the next pulse, and thereby facilitate dielectric break-down.

Figure 3:
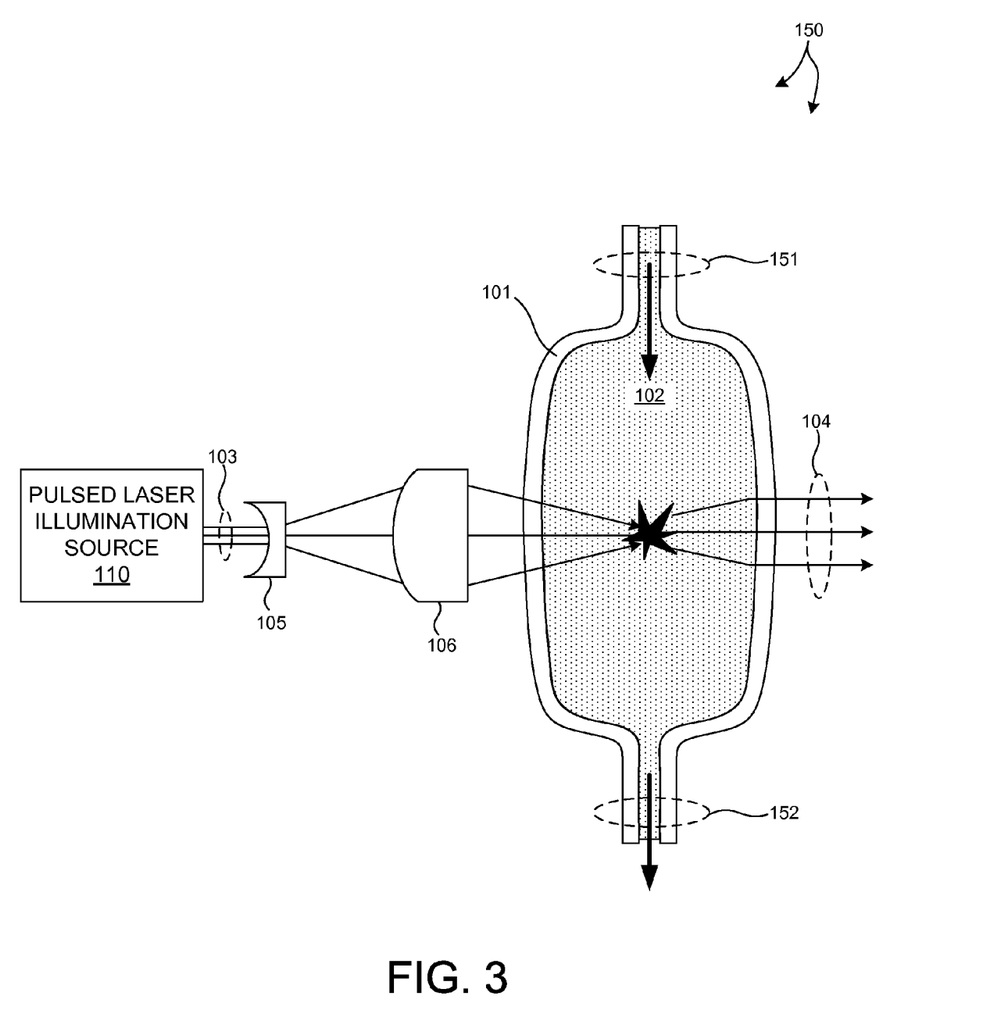
FIG. 3 is a simplified diagram illustrative of a another embodiment of the present invention including a flow of working medium through a plasma bulb.

In another further aspect, repeated plasma ignition in working medium 102 may be influenced by flowing the working medium. FIG. 3 illustrates light source 150 in another embodiment of the present invention. As illustrated in FIG. 3, light source 150 includes similar, like numbered elements described with reference to FIG. 1. However, the plasma bulb includes an entrance port 151 and an exit port 152. Working medium 102 flows through the plasma bulb during operation. In this manner, the various embodiments and examples described herein may be implemented in the context of a plasma bulb having a continuous flow of working medium through the plasma bulb itself. In some embodiments, the flow of working medium tends to sweep away "hot" working medium from the location of plasma formation at the focal point of condensing optic 106. The replacement of the "hot" working medium with "cold" working medium may allow for a shortened repetition period, and an overall increase in the flux of accessible illumination light 104.

Figure 2:
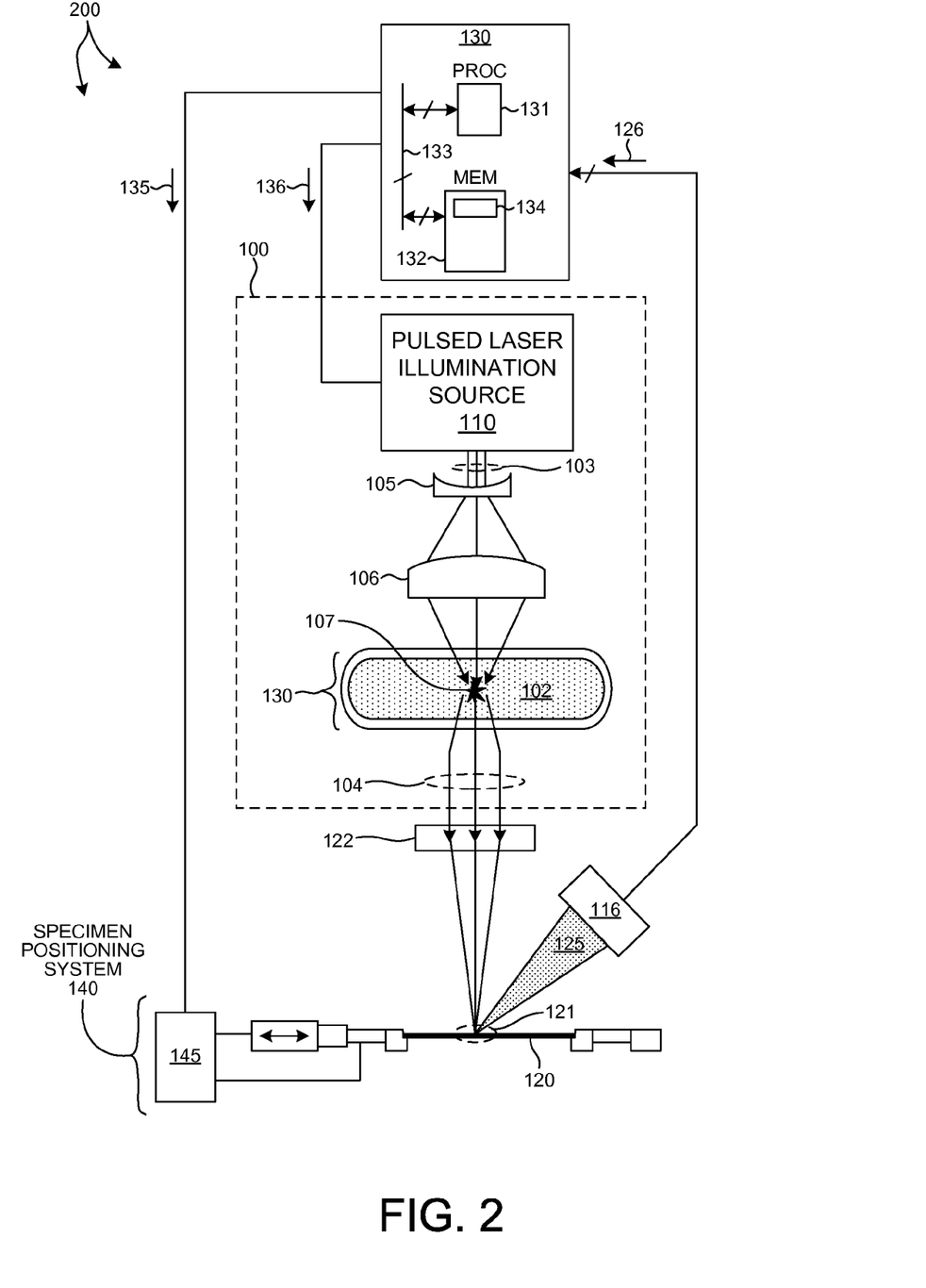
FIG. 2 illustrates a metrology tool 200 for measuring characteristics of a specimen that includes RIPLS 100 as described with reference to FIG. 1.

FIG. 2 illustrates a metrology tool 200 for measuring characteristics of a specimen that includes RIPLS 100 as described with reference to FIG. 1. As shown in FIG. 2, the system 200 may be used to perform optical scatterometry measurements over an inspection area 120 of a specimen 120 disposed on a specimen positioning system 140.

In general, and as depicted in FIG. 2, metrology system 200 includes RIPLS 100, beam shaping optics 122, and a detector 116. RIPLS 100 produces illumination light 104 incident on inspection area 121 of specimen 120. In some embodiments, the RIPLS 100 is configured to generate wavelengths between 150 nanometers and 2,500 nanometers. Beam shaping optics 122 shape and direct incident illumination light 104 to specimen 120. In some embodiments, beam shaping optics 122 collimate or focus the illumination light 104 onto inspection area 121 of specimen 120. In some embodiments, beam shaping optics 122 includes one or more collimating mirrors, apertures, monochromators, and beam stops, multilayer optics, refractive optics, diffractive optics such as zone plates, or any combination thereof.

In the embodiment depicted in FIG. 2, detector 116 collects radiation 125 from specimen 120 and generates an output signal 126 indicative of properties of specimen 120 that are sensitive to the incident illumination light 104. Radiation 125 is collected by detector 116 while specimen positioning system 140 locates and orients specimen 120. Detector 116 is able to resolve one or more photon energies and produces signals for each energy component indicative of properties of the specimen. In some embodiments, the detector 116 includes any of a CCD array, a photodiode array, a CMOS detector, and a photomultiplier tube. In some embodiments, detector 116 is a wavelength dispersive detector, for example, in embodiments of system 200 implementing wavelength dispersive metrology. In some other embodiments, detector 116 is an energy dispersive detector, for example, in embodiments of system 100 implementing energy dispersive metrology.

Metrology system 200 also includes a computing system 130 employed to acquire signals 126 generated by detector 116, and determine properties of the specimen based at least in part on the acquired signals. As illustrated in FIG. 2, computing system 130 is communicatively coupled to detector 116. In one aspect, computing system 130 receives measurement data 126 associated with measurements of specimen 120 over an inspection area 121 illuminated by illumination light 104 generated by a repeatedly induced plasma light source.

In one example, detector 116 is an optical spectrometer and measurement data 126 includes an indication of the measured spectral response of the specimen based on one or more sampling processes implemented by the optical spectrometer.

In a further embodiment, computing system 130 is configured to access model parameters in real-time, employing Real Time Critical Dimensioning (RTCD), or it may access libraries of pre-computed models for determining a value of at least one specimen parameter value associated with the specimen 120. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

As illustrated in FIG. 2, metrology tool 200 includes a specimen positioning system 140 configured to both align and orient specimen 120 with respect the illumination source 100 and detector 116 of the metrology system 200. Computing system 130 communicates command signals 135 to motion controller 145 of specimen positioning system 140 that indicate the desired position of specimen 120. In response, motion controller 145 generates command signals to the various actuators of specimen positioning system 140 to achieve the desired positioning of specimen 120.

In one further aspect, metrology tool 200 includes a computing system (e.g., computing system 130) configured to communicate command signals 136 to RIPLS 100 to synchronize the output of RIPLS 100 with the operation of another component of the metrology tool 200. Exemplary components include detector 116, a rotating element such as a rotating polarizer, rotating compensator, rotating analyzer, etc., specimen positioning system 140, or another component. In some embodiments, the output of RIPLS 100 is synchronized with the readout of a multi-sensor detector 116 (e.g., CCD array). By synchronizing the "off" period of RIPLS 100 with the readout of detector 116, mixing (i.e., smearing) of information while charges are being transferred is eliminated. In some embodiments, the output of RIPLS 100 is synchronized with the readout of a single-sensor detector 116 (e.g., photodiode).

In another further aspect, metrology tool 200 includes a computing system (e.g., computing system 130) configured to synchronize the output of RIPLS 100 with the averaging of data collected by detector 116. In some embodiments, data collected by detector 116 is averaged over a number of pulses to minimize the influence of signal noise. In some examples, the pulse repetition period of RIPLS 100 is one microsecond and data collected over 1,000 pulses is averaged. In this manner, data is averaged over one millisecond.

In yet another further aspect, metrology system 200 is configured to align and move the location of plasma 107 with respect to an illumination aperture of metrology system 200. In some embodiments, the focal point of pulsed output beam 103 is moved during the time between one or more pulses so that the illumination light 104 generated by each plasma ignition, or group of plasma ignitions, illuminates a different part of an illumination aperture (not shown) of metrology system 200. Furthermore, data collected by detector 116 is averaged over the sequence of plasma ignitions that range over the illumination aperture. For example, data collected by a detector of a beam profile reflectometer (BPR) may be spatially averaged (e.g., over a number of grating lines). In some embodiments, computing system 130 communicates command signal 136 to RIPLS 100 to move the focal point of pulsed output beam 103. In some embodiments, a scanning mirror (not shown) located in the optical beam path between pulsed laser illumination source 110 and plasma 107 is moved in response command signal 136. The scanning mirror redirects pulsed output beam 103 to different locations within the volume of working medium 102. In some embodiments, the beam steering mechanism is configured to steer the focused beam of the pulsed illumination light to different locations within the working medium such that an illumination aperture of the metrology system is sequentially filled with illumination light from a plurality of sequentially ignited plasmas. In some embodiments, the beam steering mechanism is configured to steer the focused beam of the pulsed illumination light to different locations along a direction of propagation of the focused beam. This may be desirable to align the light source with other optical elements of the metrology system. In some embodiments, the location of plasma ignition may be changed along the propagation direction by adjusting focus. In some other embodiments, the location of plasma ignition may be changed along the propagation direction by a beam steering mechanism such as a servo-controlled mirror.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the detector 116 and the RIPLS 100 in any manner known in the art. For example, the one or more computing systems 130 may be coupled to computing systems associated with the detector 116 and RIPLS 100, respectively. In another example, any of the detector 116 and the RIPLS 100 may be controlled directly by a single computer system coupled to computer system 130.

The computer system 130 of the metrology system 200 may be configured to receive and/or acquire data or information from the subsystems of the system (e.g., detector 116 and RIPLS 100, and the like) by a transmission medium that may include wireline and/or wireless portions. In this manner, the transmission medium may serve as a data link between the computer system 130 and other subsystems of the system 200.

Computer system 130 of the metrology system 200 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 200, external memory, or external systems). For example, the computing system 130 may be configured to receive measurement data (e.g., signals 126) from a storage medium (i.e., memory 132) via a data link. For instance, spectral results obtained using a spectrometer of detector 116 may be stored in a permanent or semi-permanent memory device (e.g., memory 132). In this regard, the spectral results may be imported from on-board memory or from an external memory system. Moreover, the computer system 130 may send data to other systems via a transmission medium. For instance, specimen parameter values determined by computer system 130 may be stored in a permanent or semi-permanent memory device (e.g., an external memory). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 2, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

As described with reference to FIG. 2, metrology system 200 includes an optical scatterometer system. However, in general, analysis based on one or more different metrology techniques may be contemplated within the scope of this patent document. Furthermore, measurements based on any metrology technique participating in a combined analysis may be performed on one or more individual metrology tools, one or more combined metrology tools, or any combination thereof without limitation.

In general, the broadband illumination source described herein provides useful illumination for optical metrology systems. The high brightness illumination source described herein can improve the performance of Spectroscopic Ellipsometry (SE), Spectroscopic Reflectometry (SR), and Beam-Profile Reflectometry (BPR) systems used in film, critical dimension (CD), and composition metrology. Furthermore, the high brightness illumination source described herein can improve the performance of wafer and mask inspection systems employed to detect defects of various types and sizes.

By way of non-limiting example, any of the following optical metrology techniques including, spectroscopic ellipsometry (including Mueller matrix ellipsometry), Mueller matrix spectroscopic ellipsometry, spectroscopic reflectometry, spectroscopic scatterometry, scatterometry overlay, beam profile reflectometry, (angle and polarization resolved), beam profile ellipsometry, single or multiple discrete wavelength ellipsometry, multiple angle of incidence ellipsometry, and spectroscopic polarimetry may be contemplated within the scope of this patent document.

Metrology techniques as described herein may be used to determine characteristics of semiconductor structures. Exemplary structures include, but are not limited to, FinFETs, low-dimensional structures such as nanowires or graphene, sub 10 nm structures, thin films, lithographic structures, through silicon vias (TSVs), memory structures such as DRAM, DRAM 4F2, FLASH and high aspect ratio memory structures. Exemplary structural characteristics include, but are not limited to, geometric parameters such as line edge roughness, line width roughness, pore size, pore density, side wall angle, profile, film thickness, critical dimension, pitch, and material parameters such as electron density, crystalline grain structure, morphology, orientation, stress, strain, elemental identification, and material composition.

In some embodiments, a RIPLS 100 may be implemented as part of a fabrication process tool. Examples of fabrication process tools include, but are not limited to, lithographic exposure tools, film deposition tools, implant tools, and etch tools. In this manner, the results of the metrology analysis are used to control a fabrication process. In one example, measurement data collected from one or more targets is sent to a fabrication process tool. The measurement data is analyzed and the results used to adjust the operation of the fabrication process tool.

Figure 4:
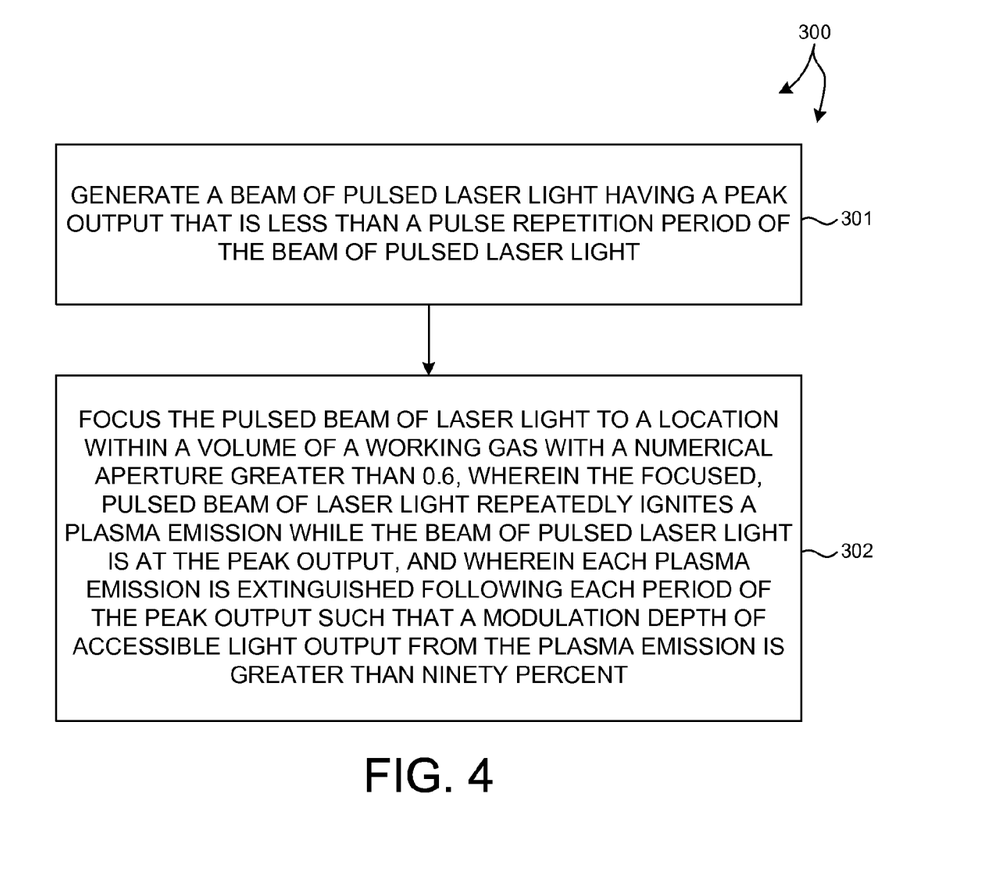
FIG. 4 is a flowchart illustrative of one exemplary method 300 suitable for generating high brightness, accessible illumination in accordance with at least one inventive aspect.

FIG. 4 illustrates a method 300 suitable for generating high brightness, accessible illumination in accordance with at least one inventive aspect. It is recognized that data processing elements of method 300 may be carried out via a pre-programmed algorithm stored as part of program instructions 134 and executed by one or more processors of computing system 130. While the following description is presented in the context of plasma bulb 130 depicted in FIGS. 1-3, it is recognized herein that the particular structural aspects of plasma bulb 130 do not represent limitations and should be interpreted as illustrative only.

In block 301, a beam of pulsed laser light is generated. The pulsed laser light has a peak output with a pulse duration of less than 20 nanoseconds. The ignition process is repeated at the repetition period, $T_R$, of the pulsed laser illumination source. Sufficient time is allowed to elapse for the previously ignited plasma to extinguish before initiating another plasma. In some embodiments, the repetition period, $T_R$, is at least 0.1 microseconds. In some embodiments, the repetition period, $T_R$, is at least 1 microsecond. In some other embodiments, the repetition period is greater than 10 ns. In some other embodiments, the repetition period is greater than 20 ns.

In block 302, the pulsed beam of laser light is focused to a location within a volume of a working medium with a numerical aperture greater than 0.6. The focused, pulsed beam of laser light repeatedly ignites plasma emission while the beam of pulsed laser light is at peak output. Each plasma emission is extinguished following each period of peak output such that a modulation depth of accessible light from the plasma emission is greater than ninety percent.

In another aspect of the present invention, the illumination source used to ignite the plasma may include one or more lasers. In a general sense, the illumination source may include any laser system known in the art. For instance, the illumination source may include any laser system known in the art capable of emitting radiation in the infrared, visible, or ultraviolet portions of the electromagnetic spectrum. In some embodiments, the illumination source includes a laser system configured to emit pulsed laser radiation. In some embodiments, the illumination source may include one or more diode lasers. For example, the illumination source may include one or more diode lasers emitting radiation at a wavelength corresponding with any one or more absorption lines of the species of the gas of the plasma cell. In a general sense, a diode laser of the illumination source may be selected for implementation such that the wavelength of the diode laser is tuned to any absorption line of any plasma (e.g., ionic transition line) or an absorption line of the plasma-producing gas (e.g., highly excited neutral transition line) known in the art. As such, the choice of a given diode laser (or set of diode lasers) will depend on the type of gas utilized in the plasma cell of the present invention.

In some embodiments, the illumination source may include one or more frequency converted laser systems. For example, the illumination source may include a Nd:YAG or Nd:YLF laser. In other embodiments, the illumination source may include a broadband laser. In other embodiments, the illumination source may include a laser system configured to emit modulated laser radiation or pulse laser radiation.

In another aspect of the present invention, the illumination source may include two or more light sources. In one embodiment, the illumination source may include two or more lasers. For example, the illumination source (or illumination sources) may include multiple diode lasers. By way of another example, the illumination source may include multiple pulsed lasers. In a further embodiment, each of the two or more lasers may emit laser radiation tuned to a different absorption line of the gas or plasma within the plasma cell.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An illumination source comprising:
   a pulsed laser operable to generate a beam of pulsed laser light having a pulse duration that is less than a pulse repetition period of the pulsed laser;
   a working medium;
   one or more beam shaping optics configured to focus the beam of pulsed laser light to a location within the working medium; and
   a computing system configured to communicate a command signal to the pulsed laser that causes the pulsed laser to adjust the pulse duration, the pulse repetition period, or both, such that a plasma emission is repeatedly ignited in the working medium by the focused beam of pulsed laser light during an on time of the beam of pulsed laser light, and wherein the plasma is repeatedly extinguished during an off time of the beam of pulsed laser light, and wherein a modulation depth of accessible light output from the plasma emission is greater than ninety percent.

2. The illumination source of claim 1, wherein the one or more beam shaping optics are configured to focus the beam of pulsed laser light to the location within the working medium with a numerical aperture greater than 0.6.

3. The illumination source of claim 1, wherein the working medium is maintained at a pressure greater than 0.5 atmospheres.

4. The illumination source of claim 1, wherein an amount of accessible light generated by the plasma has a color temperature greater than 30,000 degrees Kelvin.

5. The illumination source of claim 1, wherein a spectrum of accessible light generated by the plasma includes wavelengths from less than 200 nanometers to greater than 1,500 nanometers.

6. The illumination source of claim 1, further comprising:
   a pair of electrodes configured to preionize the working medium before an arrival of the amount of pulsed illumination light.

7. The illumination source of claim 1, further comprising:
   a second laser illumination source configured to preionize the working medium before an arrival of the amount of pulsed illumination light.

8. The illumination source of claim 1, wherein the one or more beam shaping optics include a beam expanding optic configured to expand the pulsed beam of laser light, and a condensing optic configured to focus the expanded, pulsed beam of laser light to the location within the volume of working medium.

9. The illumination source of claim 1, further comprising:
a container configured to maintain the working medium within a volume, wherein the container includes a transmissive wall that transmits the pulsed beam of laser light into the volume.

10. A metrology system comprising:
an illumination source configured to generate an amount of broadband radiation directed to a specimen, the illumination source comprising,
a pulsed laser operable to generate a pulsed beam of laser light having a pulsed duration that is less than a pulse repetition period of the pulsed laser;
a working medium, and
one or more beam shaping optics configured to focus the pulsed beam of laser light to a location within the working medium;
a computing system configured to communicate a command signal to the pulsed laser that causes the pulsed laser to adjust the pulse duration, the pulse repetition period, or both, such that a plasma emission is repeatedly ignited in the working medium by the focused, pulsed beam of laser light during an on time of the pulsed beam of laser light, and wherein the ignited plasma is repeatedly extinguished during an off time of the pulsed laser light, wherein a modulation depth of accessible light output from the plasma emission is greater than ninety percent; and
a detector configured to receive an amount of radiation collected from the specimen in response to the incident radiation and generate signals indicative of a property of the specimen.

11. The metrology system of claim 10, further comprising:
a beam steering mechanism configured to steer the focused beam of the pulsed laser light to different locations within the working medium.

12. The metrology system of claim 11, wherein the beam steering mechanism is configured to steer the focused beam of the pulsed laser light to different locations within the working medium such that an illumination aperture of the metrology system is sequentially filled with illumination light from a plurality of sequentially ignited plasmas.

13. The metrology system of claim 11, wherein the beam steering mechanism is configured to steer the focused beam of the pulsed laser light to different locations along a direction of propagation of the focused beam.

14. The metrology system of claim 11, wherein the amount of radiation collected from the specimen by the detector is averaged over the plurality of sequentially ignited plasmas.

15. The metrology system of claim 11, wherein the beams steering mechanism includes a scanning mirror located in an optical beam path between the pulsed laser and the ignited plasma.

16. The metrology system of claim 10, further comprising:
a computing system configured to synchronize a pulse of the pulsed laser with a data acquisition period of the detector.

17. The metrology system of claim 10, wherein the working medium is maintained at a pressure greater than 0.5 atmospheres.

18. The metrology system of claim 10, wherein an amount of accessible light generated by the plasma emission has a color temperature greater than 30,000 degrees Kelvin.

19. The metrology system of claim 10, wherein a spectrum of accessible light generated by the plasma emission includes wavelengths from less than 200 nanometers to greater than 1,500 nanometers.

20. The metrology system of claim 10, further comprising:
a pair of electrodes configured to preionize the working medium before an arrival of the amount of pulsed illumination light.

21. The metrology system of claim 10, further comprising:
a laser illumination source configured to preionize the working medium before an arrival of the amount of pulsed illumination light.

22. A method comprising:
generating a beam of pulsed laser light having a peak output with a pulse duration that is less than a pulse repetition period of the beam of pulsed laser light; and
focusing the pulsed beam of laser light to a location within a volume of a working medium with a numerical aperture greater than 0.6, wherein the focused, pulsed beam of laser light repeatedly ignites a plasma emission while the beam of pulsed laser light is at the peak output, and wherein each plasma emission is extinguished following each period of the peak output such that a modulation depth of accessible light output from the plasma emission is greater than ninety percent.

23. The method of claim 22, further comprising:
preionizing the working medium before an arrival of the beam of pulsed laser light at peak output.

24. The method of claim 22, wherein the working medium is maintained at a pressure greater than 0.5 atmospheres.

25. The method of claim 22, further comprising: steering the focused beam of the pulsed laser light to different locations within the working medium.

26. The method of claim 25, wherein the steering the focused beam of the pulsed laser light to different locations within the working medium involves steering the focused beam such that an illumination aperture of a metrology system is sequentially filled with illumination light from a plurality of sequentially ignited plasmas.

27. The method of claim 26, further comprising:
collecting an amount of radiation from the specimen by the detector; and
averaging the collected amount of radiation over the plurality of sequentially ignited plasmas.

28. The method of claim 25, further comprising: wherein the steering of the focused beam of the pulsed laser light involves a scanning mirror located in an optical beam path of pulsed laser light.

29. The method of claim 25, further comprising:
steering the focused beam of the pulsed illumination light to different locations along a direction of propagation of the focused beam.

30. The method of claim 25, further comprising:
Synchronizing a pulse laser light with a data acquisition period of a detector.

31. The method of claim 22, further comprising: wherein an amount of accessible light generated by the plasma emission has a color temperature greater than 30,000 degrees Kelvin.

32. The method of claim 22, further comprising: wherein a spectrum of accessible light generated by the plasma emission includes wavelengths from less than 200 nanometers to greater than 1,500 nanometers.

33. The method of claim 22, wherein the working medium is maintained at a pressure greater than 0.5 atmospheres.

34. The method of claim 22, further comprising:
   directing at least a portion of the accessible light output from the plasma emission to a specimen;
   detecting an amount of radiation collected from the specimen in response to the incident radiation; and
   generating signals indicative of a property of the specimen.

* * * * *